US00PP15940P3

(12) United States Plant Patent
Preil et al.

(10) Patent No.: US PP15,940 P3
(45) Date of Patent: Sep. 6, 2005

(54) ***RHODODENDRON* ROOTSTOCK NAMED 'RHODUNTER 37'**

(50) Latin Name: ***Rhododendron* hybrid**
Varietal Denomination: Rhodunter 37

(75) Inventors: Walter Preil, Ammersbek (DE); Rainer Ebbinghaus, Ahrensburg (DE)

(73) Assignee: Inkarho GmbH, Bad Zwischenahn (DE)

( * ) Notice: Subject to any disclaimer, the term of this patent is extended or adjusted under 35 U.S.C. 154(b) by 0 days.

(21) Appl. No.: 10/270,476

(22) Filed: Oct. 11, 2002

(65) Prior Publication Data

US 2004/0073981 P1 Apr. 15, 2004

(51) Int. Cl.[7] ..... A01H 5/00

(52) U.S. Cl. ..... Plt./239

(58) Field of Search ..... Plt./239

(56) References Cited

PUBLICATIONS

GTITM UPOVROM Citation for 'Rhodunter 37' as per PL PBR RNA0002; Jun. 8, 1998.

GTITM UPOVROM Citation for 'Rhodunter 37' as per QZ PBR 970821; Jul. 29, 1997.

*Primary Examiner*—Kent Bell
(74) *Attorney, Agent, or Firm*—Webb Ziesenheim Logsdon Orkin & Hanson, P.C.

(57) ABSTRACT

A new and distinct *Rhododendron* hybrid plant used as a rootstock that exhibits hardy and vigorous growth.

4 Drawing Sheets

Botanical classification: *Rhododendron* hybrid.
Varietal denomination: 'Rhodunter 37'.

BACKGROUND OF THE INVENTION

The present invention comprises a new and distinct cultivar of *Rhododendron* hybrid used as a rootstock known by the varietal name 'Rhodunter 37'. The new variety was discovered in Ahrensburg, Germany. The new variety is the result of a planned breeding program between an unpatented *Rhododendron fortunei* (female parent)×cv. 'Cunningham's White' (unpatented male parent). The new variety exhibits matroclinal morphological features. 'Rhodunter 37' exhibits more prominent leaf venation than both parents, but is similar in leaf color and shape to both parents. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
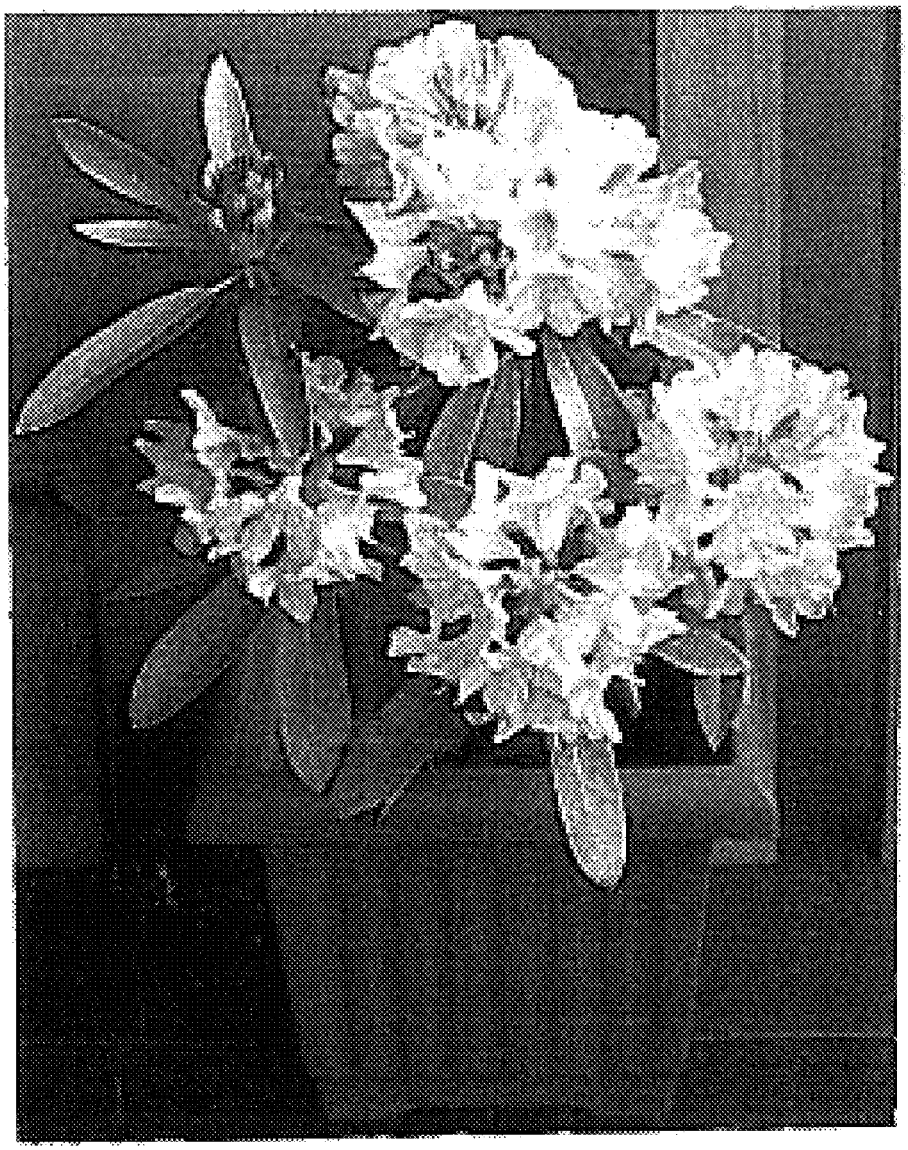
FIG. 1 shows a side perspective view of a typical flowering plant of the new variety grown to a flowering plant.
Figure 2:
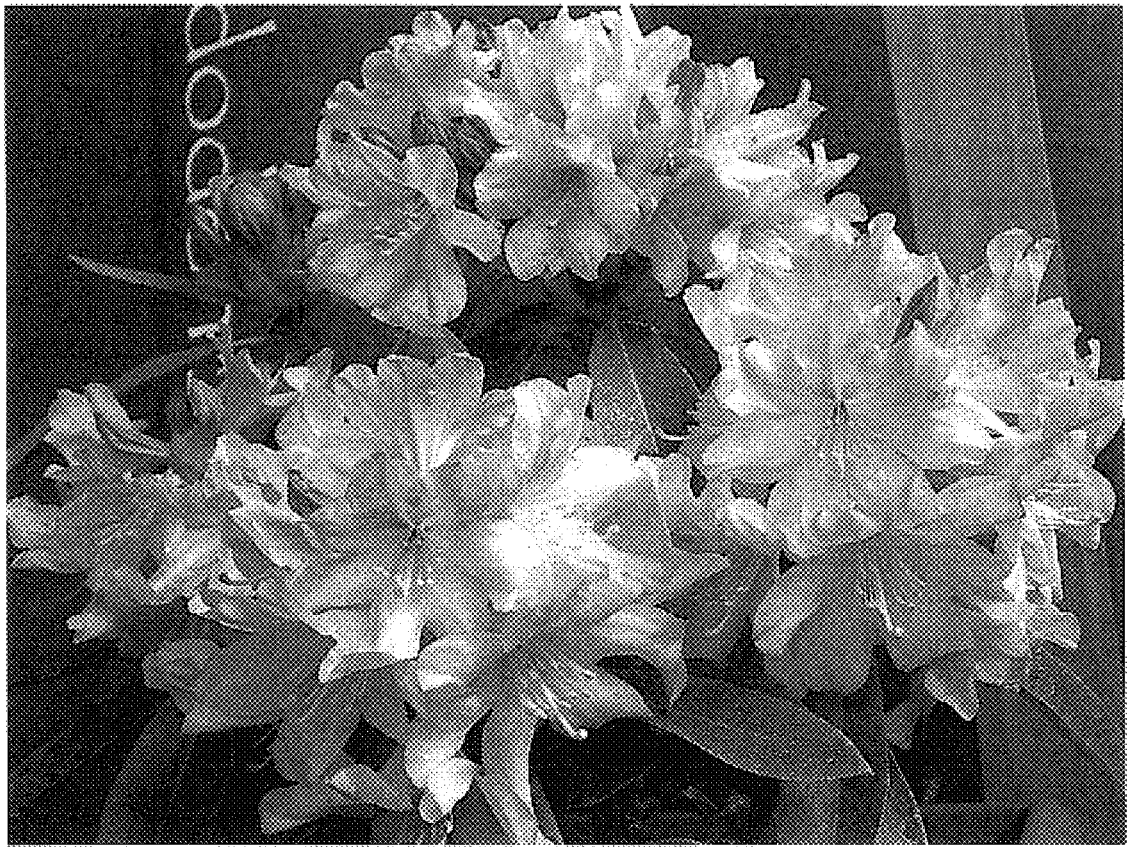
FIG. 2 shows a close-up view of the inflorescences of the new variety.
Figure 3:
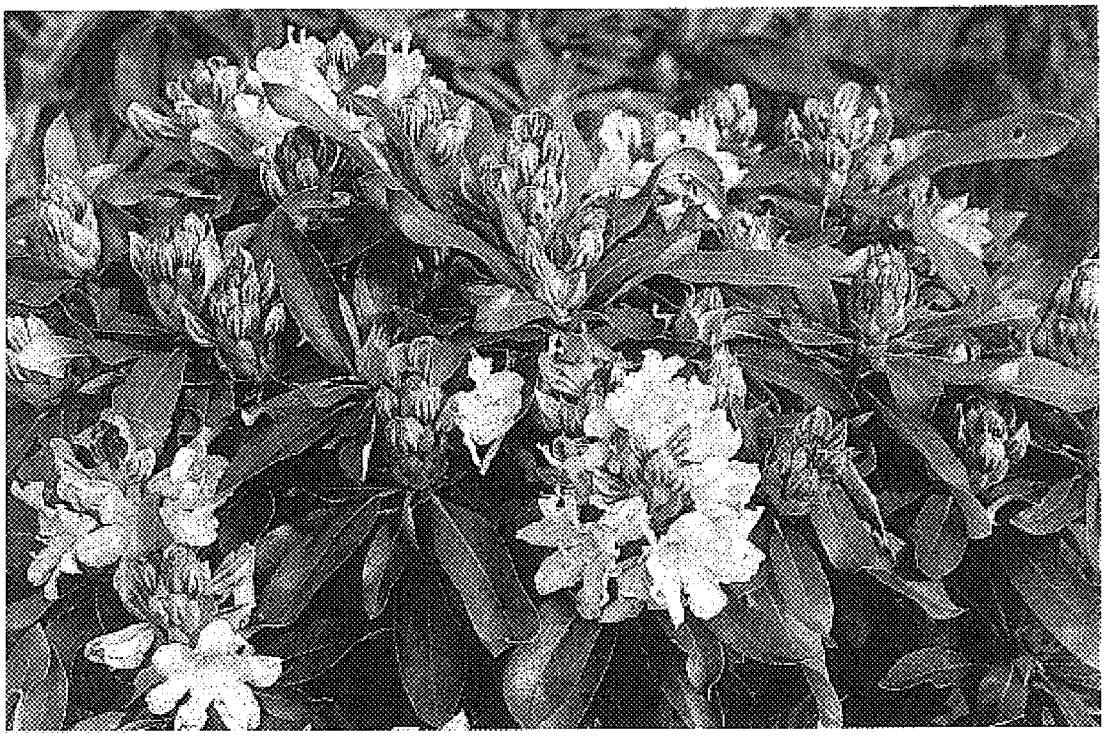
FIG. 3 illustrates the new variety with some of the flowers not open.
Figure 4:
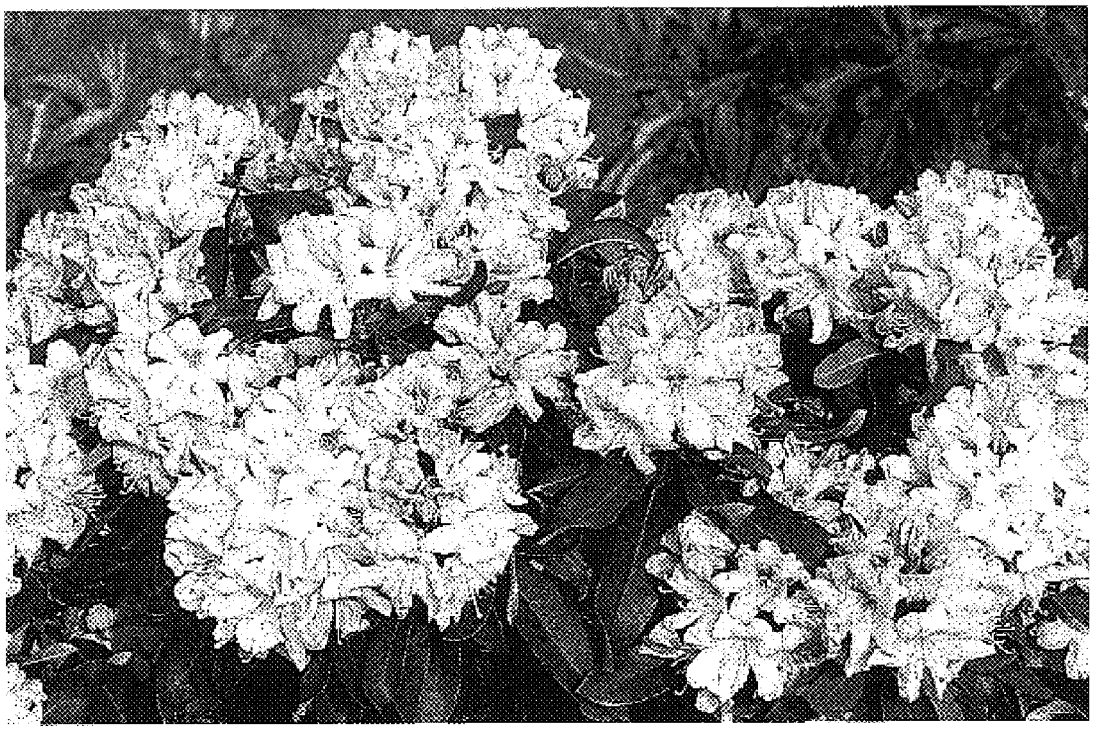
FIG. 4 illustrates the new variety with nearly all of the flowers open.

The following detailed description sets forth the characteristics of the new cultivar. The data which defines these characteristics were collected by asexual reproductions performed using tissue culture medium for shoot multiplication of *Rhododendron* species and which were carried out in Ahrensburg, Germany. The color readings were taken in natural daylight. The field-grown plants were five years old when described (unless indicated otherwise). The soil was a sandy loam mixed with peat. Color references are primarily to The R.H.S. Colour Chart of The Royal Horticultural Society of London.

PLANT

Type: Evergreen shrub.
Use: Rootstock.
Soil: Sandy loam.
Light: Full.
Fruit bearing: Very low.
Crop time: 1.5 years is required to achieve finished product size that is ready for use as a rootstock.
Dimensions at crop time (3 years after grafting. Dimensions depend on the vigor of the scion cultivar):
- *Height.*—50 cm.
- *Length.*—40 cm.

Vigor: 120% of standard using 'Nova Zembla' (unpatented) as the standard.
Habit: Erect.
Hardiness: USDA zone 6a.
Rooting habit: Compact root bales.
Time to initiate roots: 3 months at 22–25° C. for softwood cuttings.
Disease and pest resistance: No observations made to date.
Trunk (at 4 years):
- *Diameter.*—3 cm.
- *Height.*—5 cm above soil.
- *Bark color.*—Surface: Year 1: 144A. Year 2: 144A to 175A. Year 3: 175A. Year 4: 177B to 197B–197C. Flesh: 157B.
- *Lenticels.*—Inconspicous.

Branches:
*Color*.—Surface: Year 1: 144A. Year 2: 144A to 175A. Year 3: 175A. Year 4: 177B to 197B–197C. Flesh: 157B.
*Length* (*at one year*).—20 cm.
*Base diameter* (*at one year*).—7 mm.
*Texture*.—Hard.
*Internode length*.—1–2 cm.
*Branching angle at emergence*.—45° angle.
*Habit*.—Compact.
*Pubescence*.—Absent.
*Branch lenticels*.—Inconspicous.

Leaves:
*Arrangement*.—Alternate.
*Length*.—13 cm maximum.
*Width*.—4 cm maximum.
*Shape*.—Oblanceolate; with the blade occasionally undulated.
*Apex*.—Truncated.
*Base*.—Triangular.
*Color*.—Adaxial: 147A. Abaxial: 147C.
*Surface*.—Adaxial: Glabrous. Abaxial: Glabrous.
*Margins*.—Entire.
*Division*.—Undivided.
*Petiole*.—Length: 2 cm. Width: 2 mm. Color: 144A. Surface: Glabrous.
*Leaf stipules*.—Sessile.
*Leaf pubescence*.—Absent.
*Venation pattern*.—Feather-veined.
*Vein color*.—Adaxial: 144A. Abaxial: 145C.
*Leaf texture*.—Hard.
*Leaf appearance*.—Typical *Rhododendron* leaf.

Fruit: Fruits (capsules) are usually absent due to self-sterility or incompability with other *Rhododendrons*. When present, the seed color is 164B.

Flower:
*Arrangement*.—Single.
*Shape*.—Widely funnel-shaped.
*Bud*.—Shape: Oblong; Ellipsoid. Width: 20 mm. Length: 40 mm. Color: Closed: 186B. Bursting: 75B. Time of bloom: At 2 years old. Lastingness of bloom: 21 days.
*Diameter*.—8 cm.
*Depth*.—20 mm.
*Bloom quantity*.—13–17 per truss.

Petals:
*Shape*.—Fused; the corolla has a wide funnel shape.
*Number*.—7.
*Length*.—40–50 mm.
*Width of corolla*.—70–80 mm.
*Apex*.—Round.
*Margin*.—Slightly undulated.
*Color*.—When opened: Upper surface: 69 A to 69 D. Lower surface: 69 A. Before bud burst: Lower surface: 73 B to 73 C.
*Peduncle*.—Length: 4 cm. Width: 3 mm. Surface: Glabrous. Color: Green when flowers are fully open.

Sepals: Not present.

Petaloids: Not present.

Natural flowering season: Beginning of May through the end of May.

Fragrance: Inconspicuous.

REPRODUCTIVE ORGANS

Stamens:
*Number*.—14.
*Length*.—30 mm.
*Color*.—150D.

Anthers:
*Shape*.—Normal *Rhododendron* type.
*Color*.—158B.
*Length*.—25 mm.
*Width*.—1 mm.
*Amount of pollen*.—Medium.
*Color of pollen*.—150D.
*Stigma color*.—145A.

Pistil:
*Length*.—5 cm.
*Number*.—1.

Style:
*Color*.—159D.
*Length*.—45 mm.
*Width*.—1 mm.

Ovaries:
*Length*.—5 mm.
*Width*.—3 mm.
*Color*.—137C.
*Position*.—Superior.

I claim:

1. A new and distinct variety of *Rhododendron* hybrid plant, as illustrated and described.

* * * * *